(12) United States Patent
Akashe et al.

(10) Patent No.: US 6,376,482 B2
(45) Date of Patent: Apr. 23, 2002

(54) USE OF MESOPHASE-STABILIZED COMPOSITIONS FOR DELIVERY OF CHOLESTEROL-REDUCING STEROLS AND STANOLS IN FOOD PRODUCTS

(75) Inventors: Ahmad Akashe, Mundelein; Miranda Miller, Arlington Heights, both of IL (US)

(73) Assignee: Kraft Foods, Inc., Northfield, IL (US)

( * ) Notice: Subject to any disclaimer, the term of this patent is extended or adjusted under 35 U.S.C. 154(b) by 0 days.

(21) Appl. No.: 09/859,173

(22) Filed: May 16, 2001

Related U.S. Application Data

(62) Division of application No. 09/258,759, filed on Feb. 26, 1999.

(51) Int. Cl.[7] .......................... A23L 1/035; A61K 31/56
(52) U.S. Cl. ...................... 514/182; 426/601; 426/602; 426/604; 426/611
(58) Field of Search ................... 514/182; 426/601, 426/602, 604, 611

(56) References Cited

U.S. PATENT DOCUMENTS

| | | | |
|---|---|---|---|
| 3,865,939 A | 2/1975 | Jandacek | 424/238 |
| 4,112,218 A | 9/1978 | Inoue et al. | 536/5 |
| 4,115,313 A | 9/1978 | Lyon et al. | 252/309 |
| 4,137,338 A | 1/1979 | Gawrilow | 426/601 |
| 4,160,850 A | 7/1979 | Hallstrom et al. | 426/601 |
| 5,156,866 A | 10/1992 | Sato et al. | 426/5 |
| 5,244,887 A | 9/1993 | Straub | 514/182 |
| 5,445,811 A | 8/1995 | Norrlind et al. | 424/9.4 |
| 5,502,045 A | 3/1996 | Miettinen et al. | 514/182 |
| 5,652,011 A | 7/1997 | Heertje et al. | 426/601 |
| 5,707,670 A | 1/1998 | Mehansho et al. | 426/73 |
| 5,736,177 A | 4/1998 | McGinley et al. | 426/96 |
| 5,747,464 A | 5/1998 | See | 514/26 |
| 5,766,627 A | 6/1998 | Sankaram et al. | 424/450 |
| 5,807,572 A | 9/1998 | Kim et al. | 424/450 |

FOREIGN PATENT DOCUMENTS

| | | |
|---|---|---|
| EP | 0 289 636 A1 | 11/1988 |
| EP | 0 558 523 B1 | 7/1994 |
| EP | 0 898 896 A1 | 3/1998 |
| EP | 0 839 458 A1 | 6/1998 |
| EP | WO 98/28990 | 7/1998 |
| EP | 0 897 671 A1 | 2/1999 |
| EP | 0 897 970 A1 | 2/1999 |
| EP | 0 897 971 A1 | 2/1999 |

OTHER PUBLICATIONS

"Reduction of Serum Cholesterol with Sitostanol–Ester Margarine in a Mildly Hypercholesterolemic Population", Tatu A. Mietten, M.D., Pekka Puska, M.D., Helena Cylling, M.D., Hannu Vanhanen, M.D. and Erkki Vartianen, M.D., *The New England Journal of Medicine*, vol. 333, No. 20, Nov. 16, 1995, pp. 1308–1312.

*Primary Examiner*—S. Mark Clardy
(74) *Attorney, Agent, or Firm*—Fitch, Even, Tabin & Flannery

(57) ABSTRACT

Plant sterols and plant sterol esters have been shown to be cholesterol-reducing agents in human serum. In the present invention, plant sterols, plant stanols, plant sterol esters, and plant stanol esters are incorporated into mouthfeel-enhancing, texture-building and composition-stabilizing compositions which are mesophase-stabilized compositions for use in low-fat, fat-free and triglyceride-free food products. Such compositions may be incorporated into food products resulting in low-fat, fat-free and triglyceride-free food products which may be used to deliver a recommended daily dosage of the cholesterol-reducing compounds to segments of the population which must limit it's cholesterol intake.

41 Claims, No Drawings

USE OF MESOPHASE-STABILIZED COMPOSITIONS FOR DELIVERY OF CHOLESTEROL-REDUCING STEROLS AND STANOLS IN FOOD PRODUCTS

This is a division of prior application Ser. No. 09/258,759, filed Feb. 26, 1999, which is hereby incorporated herein by reference in its entirety. The entire disclosure of the prior application, from which a copy of the oath or declaration is supplied under paragraph 3 below, is considered as being part of the disclosure of the accompanying application, and is hereby incorporated by reference therein.

FIELD OF THE INVENTION

The present invention relates to low-fat, fat-free and triglyceride-free food products which incorporate plant sterols, plant stanols, plant sterol esters, and plant stanol esters as cholesterol-reducing agents in low-fat, fat-free and triglyceride-free foods. These cholesterol-reducing agents are incorporated into mouthfeel-enhancing, texture-building, emulsion-stabilizing and dispersion-stabilizing compositions which are mesophase-stabilized compositions for use in low-fat, fat-free and triglyceride-free food products.

BACKGROUND OF THE INVENTION

Cholesterol has been known for many years to be a component of atherosclerotic plaques. Mounting evidence indicates diets high in cholesterol may increase the levels of cholesterol in the blood which, in turn, increase the risk of atherosclerotic disease and its attendant manifestations of heart attack, stroke and other tissue injuries resulting from atherosclerosis. Cholesterol absorbed from dietary sources is thought to increase the risk of atherosclerotic disease.

Other than avoidance or reduced consumption of high cholesterol foods, measures available without prescription to the general public to reduce the absorption of cholesterol from the diet have met with little success. However, high cholesterol levels in serum can be lowered effectively by altering the intestinal metabolism of lipids. In recent years, it has become known that certain plant sterols and plant stanols such as β-sitosterol (24-ethyl-5-cholestene-3β-ol) and its hydrogenated form β-sitostanol (24-ethyl-5α-cholestane-3β-ol) can help lower serum cholesterol by inhibiting cholesterol absorption. Plant stanols are the hydrogenated form of plant sterols. See, e.g., "Reduction of Serum Cholesterol With Sitostanol-ester Margarine in a Mildly Hypercholesterolemic Population", *New England Journal of Medicine*, Nov. 16, 1995 pp. 1308–1312.

For purposes of this invention, "plant sterols" is intended to include both plant sterols and plant stanols; the term "sterols" alone is intended to include only the plant sterols; and the term "stanols" alone is intended to include only the plant stanols. Likewise, for purposes of this invention, "plant sterol esters" is intended to include both plant sterol esters and plant stanol esters; the term "sterol esters" alone is intended to include only the plant sterol esters; and the term "stanol esters" alone is intended to include only the plant stanol esters. For purposes of this disclosure, a "cholesterol-reducing-compound" is defined as either a plant sterol or a plant sterol ester as defined herein.

For purposes of this invention, "emulsifier mixture" is intended to include one of three different possible emulsifier mixtures: (1) a mixture of emulsifier A which has an HLB ranging from about 6 to about 9, emulsifier B which has an HLB ranging from about 2 to about 6, and emulsifier C which has an HLB ranging from about 9 to about 22; (2) a mixture of emulsifier A which has an HLB ranging from about 6 to about 9 and emulsifier C which has an HLB ranging from about 9 to about 22; and (3) a mixture of emulsifier B which has an HLB ranging from about 2 to about 6 and emulsifier C which has an HLB ranging from about 9 to about 22.

The use of plant sterols in food products is considered safe, since plant sterols are natural components of vegetable fats and oils. Plant sterols themselves are not absorbed—or only absorbed in very small amounts—from the intestines. A decreased incidence of coronary disease is clearly associated with a decrease in serum cholesterol and, in particular, a decrease in LDL cholesterol. A high serum cholesterol value is one of the most significant indicators of risk of coronary disease. There are a variety of naturally occurring plant sterols which have been reported to have a cholesterol-reducing effect, although not all have equivalent action. The mechanism by which plant sterols achieve this effect has not been fully elucidated.

In recent years, many efforts have been made to reduce the fat content of various foods, such as salad dressing, sour cream and frozen desserts. When the fat level is reduced in conventional food products, however, the organoleptic properties are generally adversely affected because of the oiliness (lubricity) and slipperiness imparted by the fat particles suspended in the food product are effectively lost.

Other mouthfeel and textural properties such as richness and creaminess may also be adversely affected by removal or reduction of fat. Polysaccharide and protein ingredients commonly known as fat mimetics have been used to restore some of the textural properties contributed by emulsified fats and oils, such as viscosity and gel strength. They have been used less successfully to restore more subtle mouthfeel factors. In addition, many of these ingredients have negative impact on flavor, another key aspect of product quality. The FDA Standards of Identity recognize "reduced-fat" foods as foods that have 25% less fat than the market standard of a full-fat counterpart of that food type. "Light" products retain 50% less fat than the market standard of a full-fat serving of that food type. "Low-fat" foods are defined as having less than 3 grams of fat per serving, and "fat-free" foods have less than ½ gram fat per serving.

For purposes of this invention, the term "low-fat" includes "reduced-fat," "light," "low-fat," and "fat-free" as defined by the FDA Standards of Identity. In addition, for purposes of this invention, "low-fat" also encompasses triglyceride-free products although they are not included in the FDA Standards of Identity. However, the term "fat-free" is intended to include only "fat-free" as defined by the FDA Standards of Identity. In addition, the terms "low-fat" and "fat-free" are intended to include low-fat and fat-free food products that do not fall into the categories defined by the FDA Standards of Identity (as of the time of this disclosure) but deliver to the consumer reduced levels of fat per serving. Furthermore, through the use of higher levels of plant sterol esters, even if no oil is added in a formulation of the described compositions, while such a composition may not be termed "fat-free", the term "triglyceride-free" is an accurate description of such formulations utilized in this disclosure.

Low-fat and fat-free food products have been developed which duplicate the viscosity and other textural attributes of the missing fat by means of suitable food polymers, such as gums (xanthan or alginate), cellulose and its derivatives, starches and various microparticulated polymeric complexes. Unfortunately, such additives generally cannot provide the desired organoleptic characteristics normally associated with full-fat products, namely flavor, mouthfeel and thermal factors.

Many of these desired attributes associated with full-fat products are due to the presence of two distinct phases—an aqueous phase and an oil phase. The oil phase provides a reservoir of solvent for the flavor chemicals to dissolve in. By altering the proportions of the two phases, the partitioning of the flavor chemicals between the two phases is changed, affecting the character of the flavor and the way it is released in the mouth. In the extreme example of a fat-free product, the product consists of a single phase, and the flavor chemicals are dispersed in the aqueous phase. Free oil typically contributes to the mouthfeel of full-fat products. In the mouth, some free oil separates from the bulk of the product, coats the mouth, and provides oily lubricity. Fats and oils also contribute thermal sensations in the mouth. These effects can be either mouthwarming as a result of the coating of the free oil, or mouthcooling due to melting of any crystalline fat.

The cholesterol-reducing-compound-containing mesophase-stabilized compositions which are provided by the present disclosure significantly improve the quality of low-fat and fat-free food products by providing some of the aforementioned missing attributes. They do this by providing a separate phase, a mesophase, which is neither an aqueous phase nor an oil phase, but a liquid crystalline phase of both hydrophobic and hydrophilic character. They also provide a way of potentiating or maximizing the oily and fatty attributes of whatever oils or fats exist in the low-fat or fat-free product. By light microscopy, the mesophase-stabilized emulsions contain oil droplets which appear in a narrow range of sizes as relatively small-sized oil droplets dispersed in an aqueous gel phase. Upon centrifugation, most of the mesophase-stabilized emulsions of the present invention separate into an oil emulsion and a mesophase gel. In a food product, the oil droplets of the emulsion phase release their oil, providing lubricity, flavor delivery, and mouthwarming.

The mesophase gel provides stability and structure to the food product. Because starch components and other stabilizing or thickening agents are not required to structure the food product, maximum oily mouthfeel and flavor characteristics are retained. In fact, any fats or oils present in the mesophase-stabilized emulsions or mesophase-stabilized dispersions are potentiated by the present invention. The present invention represents a new method for introducing plant sterols and plant sterol esters into low-fat and fat-free food products by allowing highly viscous emulsions and dispersions to be made regardless of the oil level, with no requirement for polymeric protein or polysaccharide thickening or bulking ingredients. Additionally, the compositions of the present invention permit the introduction of cholesterol-reducing compounds into the diet in a highly effective manner.

Conventionally, plant sterols have been incorporated into food products by melting a sterol or stanol, incorporating it into an oil phase, and blending the oil phase with other components to result in a plant sterol-containing food product. However, the plant sterols have high melting points, about 100–180° C., which result in the crystallization of the plant sterols within the oil phase of such food products. Such crystallization of the plant sterols within the oil phase results in a gritty texture attributed to the food product into which the oil/plant sterol phase is incorporated. This gritty texture is especially detectable when the oil/plant sterol phase is incorporated at high levels in the food products. However, esterification of plant sterols results in lower melting points of the plant sterol esters, usually about 16° C. to about 90° C. Thus, the plant sterol esters are less likely to crystallize during manufacture of food products and are, therefore, the more preferred form of the cholesterol reducing agents. However, most plant sterol esters will crystallize in the food product unless their melting point is below the storage temperature of the food product into which they are incorporated. Although the use of plant sterol esters allows for improved incorporation in food products (as compared to the plant sterols with higher melting temperatures), it would still be desirable to have alternative methods of incorporating plant sterols and/or plant sterol esters into low-fat and fat-free food products. The present invention provides such methods.

This invention uses mesophase-stabilized compositions to incorporate plant sterols and/or plant sterol esters in a variety of food products. By incorporating the plant sterols and/or plant sterol esters into low-fat and fat-free food products by use of a mesophase, the cholesterol-reducing-compounds are effectively dispersed as individual molecules in the mesophase structure and thus reduce the tendency to crystallize. Moreover, since the plant sterols and/or plant sterol esters form an integral part of the mesophase structure, it is not necessary to incorporate them into food products by using an oil carrier Any excess (i.e., any that is not dispersed into the mesophase) plant sterols or plant sterol esters can be readily dispersed as an emulsion in the mesophase by using high shear (e.g., about 5000 $sec^{-1}$ to about 50,000 $sec^{-1}$). Thus, the plant sterols or plant sterol esters may be incorporated as an integral part of the mesophase and/or as an emulsion stabilized by the mesophase.

This invention allows larger amounts of plant sterols and/or plant sterol esters to be incorporated in low-fat or fat-free food products without adversely affecting the organoleptic properties. In fact, the use of a mesophase to incorporate plant sterols and plant sterol esters can actually improve the organoleptic properties of the resulting food products and can result in new product concepts. Creamy mesophase-stabilized emulsions may be made with as much as 10 percent stanols, 10 percent sterols, 30 percent stanol ester, or 50 percent sterol ester. Since the plant sterols and/or plant sterol esters are incorporated without the need for an oil carrier, lower fat products can easily be created. In addition, the biological attributes of the plant sterols and/or plant sterol esters are enhanced when incorporated using the mesophase of the present invention. Since the plant sterols and plant sterol esters appear to be contained as molecular inclusions in the mesophase structure, they are delivered to the intestine in a form similar to that when cholesterol is emulsified in bile-salt micelles and delivered to the intestines. This enhanced delivery system should allow the currently recommended dosage of about 3 g/day to be achieved in an easier and more acceptable form for the consumer.

It is an object of the present disclosure to provide low-fat and fat-free food products which incorporate plant sterols and/or plant sterol esters as cholesterol-reducing agents in low-fat and fat-free foods. The cholesterol-reducing agents are incorporated into mouthfeel-enhancing, texture-building, emulsion-stabilizing and dispersion-stabilizing compositions which are mesophase-stabilized emulsions and dispersions for use in low-fat and fat-free food products. Using the present system, high levels of these agents can be used in food products without adversely affecting the organoleptic properties of the food products.

It is a further object of the present disclosure to provide methods for making low-fat and fat-free food products containing plant sterols and/or plant sterol esters as cholesterol-reducing agents. These methods generate mouthfeel-enhancing, texture-building, emulsion-stabilizing and dispersion-stabilizing compositions which are cholesterol-reducing-compound-containing mesophase-stabilized compositions for use in low-fat and fat-free food. These and other objects and advantages of the present invention will be apparent to those skilled in the art upon consideration of the present disclosure.

SUMMARY OF THE INVENTION

The present invention relates to cholesterol-reducing agents and their incorporation into low-fat and fat-free food products using mesophase-stabilized compositions. Such mesophase-stabilized compositions include both mesophase-stabilized emulsion compositions for use in low-fat and triglyceride-free food products and mesophase-stabilized dispersions for use in fat-free food products. The mesophase-stabilized compositions are prepared using plant sterols and/or plant sterol esters and a mixture of either two or three different emulsifiers. The two emulsifier mesophase-stabilized compositions are comprised of either emulsifiers A and C or emulsifiers B and C. The three emulsifier mesophase-stabilized compositions are comprised of emulsifiers A, B and C Emulsifier A has an intermediate hydrophilic/lipophilic balance (HLB). Emulsifier B has a relatively low HLB. Emulsifier C has a relatively high HLB. The mesophase-stabilized compositions made with plant sterols and plant sterol esters are highly viscous, even at low oil levels for the emulsions, and in the absence of polymeric protein or polysaccharide thickening or bulking ingredients. The mesophase-stabilized compositions can be used to formulate stable, viscous food products which have excellent lubricity, mouthfeel and flavor characteristics. These cholesterol-reducing-compound-containing mesophase-stabilized emulsions are especially useful in low-fat and triglyceride-free food products. In addition, the mesophase-stabilized dispersions are especially useful in fat-free food products. The basic mesophase-stabilized compositions are more fully described in our copending application entitled "MESOPHASE-STABILIZED EMULSIONS AND DISPERSIONS FOR USE IN LOW-FAT AND FAT-FREE FOOD PRODUCTS," which was filed on the same date as this present application and which is hereby incorporated by reference in its entirety.

It is well known that plant sterols and plant sterol esters help to lower serum cholesterol. Because the melting point of plant sterol esters is so much lower than that of plant sterols, and therefore less likely to crystallize when incorporated into food products, the use of plant sterol esters for the formation of the disclosed compositions is generally preferred.

Although not wishing to be limited by theory, it is believed that plant sterols and plant sterol esters interfere with cholesterol absorption by competition-type mechanisms. Cholesterol absorption takes place primarily in the proximal third of the small intestine. Cholesterol esters must be converted to their free hydroxyl form by the action of cholesterol esterases before they can be absorbed. The free cholesterol requires bile salts for solubilization and absorption. Bile salts form an aqueous dispersion of micelles in which the cholesterol is solubilized along with phospholipids and hydrolysis products of other dietary lipids. Micelles transport the cholesterol across the hydrophilic barrier the unstirred water layer) to reach the surface of the intestinal mucosa. At the mucosa, it is thought that the cholesterol dissociates from the micelle and is transported into the mucosal cells by a process which has not yet been defined (possibly passive exchange diffusion or by protein-mediated transport). Plant sterols could interfere with the above mechanism of cholesterol absorption at either of, or at both of, the following steps: (a) they could compete with cholesterol for absorption into the bile-salt micelles or (b) they could compete with the transport mechanism into the mucosal cells. Whether plant sterols displace cholesterol from the micelles by mass action, or whether they compete with cholesterol for binding at the mucosal transport system, a soluble form of the plant sterol should be more effective than crystalline forms. In fact, it has been suggested that "the cholesterol-lowering effect of sitostanol may be increased when it is ingested in a soluble form." *New England Journal of Medicine*, Nov. 16, 1995, p. 1308.

Largely due to the high melting point of plant sterols, in most conventional methods for incorporation of plant sterols into food products, much of the plant sterols are in the crystalline form. Even when dissolved in an oil phase, they tend to form crystals. Therefore, only a small portion of the plant sterols are available in the intestines to compete with cholesterol for the mixed bile-salt micelles. The nonsoluble fraction of the plant sterol would pass through the gut intact, and thus, unabsorbed. In contrast, plant sterols and plant sterol esters incorporated into a mesophase appear to remain, to a large extent, solubilized. In this form, they can readily be exchanged with micellar cholesterol and can effectively compete for cholesterol either at the micelle or at the mucosal surface. In addition, plant sterols esters and/or plant sterols that are not incorporated into the mesophase may contribute to the formation of a mesophase-stabilized emulsion, which may also contribute to the absorption of plant sterol esters and/or plant sterols by the intestinal mucosa.

The present invention includes cholesterol-reducing-compound-containing mesophase-stabilized compositions for use in low-fat and fat-free food products. These mesophase-stabilized compositions include about one to about fifty percent of a cholesterol-reducing-compound, an aqueous phase and about one to about fifteen percent of an emulsifier mixture comprising a combination of emulsifiers selected from the group consisting of (1) emulsifier A, B, and C; (2) emulsifiers A and C; and (3) emulsifiers B and C in an emulsifier mixture and an aqueous phase.

The present invention also includes methods for making such cholesterol-reducing-compound-containing mesophase-stabilized compositions for use in low-fat and fat-free food products. One such method comprises (a) dispersing an emulsifier mixture in an aqueous solution to form an aqueous emulsifier phase; (b) heating the aqueous emulsifier phase to a temperature of about 45° C. to about 90° C.; (c) melting a cholesterol-reducing compound; (d) adding the melted cholesterol-reducing compound to the heated aqueous emulsifier phase with mixing; (e) cooling the aqueous emulsifier phase containing the cholesterol-reducing compound to a temperature of about 20° C. to about 90° C.; (f) subjecting the cooled aqueous emulsifier phase containing the cholesterol-reducing-compound to high shear of about 5000 sec$^{-1}$ to about 50,000 sec$^{-1}$ to form a homogenized mesophase composition; (g) cooling the homogenized mesophase composition to a temperature of about 3° C. to about 25° C. to form the cholesterol-reducing-compound-containing mesophase-stabilized composition.

Another method for making such cholesterol-reducing-compound-containing mesophase-stabilized compositions for use in low-fat and fat-free food products comprises (a) dispersing an emulsifier mixture in an aqueous solution to form an aqueous emulsifier phase; (b) heating the aqueous emulsifier phase to a temperature of about 45° C. to about 90° C.; (c) melting a cholesterol-reducing-compound; (d) adding the melted cholesterol-reducing compound to the heated aqueous emulsifier phase with mixing; (e) heating or maintaining the aqueous emulsifier phase containing the cholesterol-reducing compound at a temperature of about 80° C. to about 100° C. for a time sufficient to form a mesophase-stabilized composition; (f) slowly cooling the product of step (e) to a temperature of about 60° C. to about 75° C. with mixing; (g) subjecting the cooled mixture from step (f) to high shear of about 5000 sec$^{-1}$ to about 50,000 sec$^{-1}$ to form the cholesterol-reducing-compound-containing mesophase-stabilized composition.

The present invention also includes a cholesterol-reducing-compound-containing mesophase-stabilized emulsion for use in low-fat food products, said mesophase-stabilized emulsion comprising about 5 percent to about 50 percent of a cholesterol-reducing compound, about one to about fifteen percent of an emulsifier mixture an aqueous phase, and an oil phase.

The present invention also includes a method for making a cholesterol-reducing-compound-containing mesophase-stabilized composition comprising three emulsifiers, an aqueous phase, an oil phase and a cholesterol-reducing compound for use in low-fat food products, said method comprising (a) dispersing an emulsifier mixture in an aqueous phase to form an aqueous emulsifier phase; (b) heating the aqueous emulsifier phase to a temperature of about 60° C. to about 90° C.; (c) melting the cholesterol-reducing compound in the oil phase; (d) adding the oil phase-containing the cholesterol-reducing compound to the aqueous emulsifier phase at a temperature in the range of about 75° C. to about 90° C. with mixing to form the coarse mesophase-stabilized emulsion; (e) subjecting the product of step (d) to shear of about 5000 sec$^{-1}$ to about 50,000 sec$^{-1}$ to form a cholesterol-reducing-compound-containing mesophase-stabilized emulsion; and (f) cooling the cholesterol-reducing-compound-containing mesophase-stabilized emulsion formed to a temperature of about 3° to about 20° C. The high shear step provides oil droplets which are reduced in size and fall into in a narrow size range which increases the stability of the cholesterol-reducing-compound-containing mesophase-stabilized emulsion.

The present invention also includes a method for making a cholesterol-reducing-compound-containing mesophase-stabilized composition comprising three emulsifiers, an aqueous phase, an oil phase, and a cholesterol-reducing compound for use in low-fat food products. This method comprises(a) adding an emulsifier mixture selected from the group consisting of (1) emulsifiers A and B; (2) emulsifier A and (3) emulsifier B to the oil phase at a temperature of about 60° C. to about 95° C. with mixing to form an oil emulsion phase; (b) adding the cholesterol-reducing compound to the oil emulsifier phase; (c) adding Emulsifier C to the aqueous phase to form an aqueous emulsifier phase, (d) adding the oil emulsifier phase to the aqueous emulsifier phase to form a coarse emulsion, and (e) subjecting the coarse emulsion to shear at about 5000 sec$^{-1}$ to about 50,000 sec$^{-1}$ for a time sufficient to form the cholesterol-reducing-compound-containing mesophase-stabilized composition.

DETAILED DESCRIPTION OF THE INVENTION

The present invention provides low-fat, fat-free and triglyceride-free food products which incorporate plant sterols and/or plant sterol esters as cholesterol-reducing compounds. Preferably, the plant sterol esters are employed. These cholesterol-reducing compounds are incorporated into mouthfeel-enhancing, texture-building, emulsion-stabilizing and dispersion-stabilizing compositions which are mesophase-stabilized compositions for use in low-fat, fat-free and triglyceride-free food products and methods for making such compositions. Such food products include pourable dressings, spoonable dressings, whipped desserts, whipped toppings, frozen dairy foods, dips, sauces, yogurts, dessert toppings, spreads, sour cream products, cream cheese products, and the like. In one embodiment of the invention, the composition is a mesophase-stabilized emulsion including one or more cholesterol-reducing compounds, at least two or three emulsifiers selected with proper HLB values, an oil phase, and an aqueous phase. Such a mesophase-stabilized emulsion can be prepared by adding either (1) emulsifiers A (which has an HLB value of about 6 to about 9) and B (which has an HLB value of about 2 to about 6); (2) emulsifier A or, (3) emulsifier B, to an oil phase, heating the oil phase to melt and dissolve the emulsifiers and form an oil emulsifier phase. Then one or more cholesterol-reducing compounds is added to the oil emulsifier phase. Emulsifier C, which has an HLB of about 9 to about 22, is added to the aqueous phase to form an aqueous emulsifier phase. The oil emulsifier phase and the aqueous emulsifier phase are then mixed, then subjected to shear of about 5000 sec$^{-1}$ to about 50,000 sec$^{-1}$, and then cooled. This process results in a mesophase-stabilized emulsion which has cholesterol-reducing characteristics which is useful in the manufacture of low-fat food products. Although not required, it is generally preferred that the two or three emulsifiers are added to their respective oil and aqueous phases as powders. For emulsifiers melting at or close to ambient temperature, such powders can be prepared, if desired, by grinding the emulsifiers at temperatures below their melting points; of course, such powders must be maintained at such temperatures until they are actually added to their respective oil or aqueous phases. In important embodiments of the invention, Emulsifier A is a diacetyl tartaric acid ester of monoglyceride (DATEM); Emulsifier B; monoglyceride, and emulsifier C is sodium stearoyl lactylate (SSL).

In another important embodiment, a cholesterol-reducing mesophase gel is formed using one or more cholesterol-reducing compounds and at least three emulsifiers dispersed in an aqueous phase. This mesophase gel, which does not contain oil, may be used to form mesophase-stabilized emulsions and dispersions by use of high shear. An emulsifier mixture selected from the group comprising (1) emulsifiers A, B, and C, (2) emulsifiers A and C, and (3) emulsifiers B and C, is added to an aqueous phase with mixing. The mixture is subjected to high shear ranging from about 5000 sec$^{-1}$ to about 50,000 sec$^{-1}$. This process results in a mesophase gel which has cholesterol-reducing characteristics which is useful in the manufacture of fat-free, triglyceride-free and low-fat food products.

Other ingredients such as egg products, salt, sugar, and edible acids can be added or incorporated into the mesophase-stabilized emulsions or dispersions to form mesophase-stabilized fat-free, triglyceride-free or low-fat food products. Egg products may be used in any of the embodiments of the present invention and may be egg yolk, salted egg yolk, whole eggs, liquid egg product, spray-dried egg yolk, spray dried whole egg, or any other form of egg product. Of course, it will generally be preferred that low or lower cholesterol-containing egg products be used. Likewise edible acids may be used in the present invention, examples of such edible acids include, for example, vinegar, lemon juice, lime juice, acetic acid, phosphoric acid, lactic acid, citric acid, mixture thereof, and similar acids known in the art. For example, a spoonable dressing product can be prepared by mixing such a mesophase-stabilized emulsion with egg yolk, salt, sugar, and edible acid; the resulting spoonable dressing is stable at room temperature.

When preparing mesophase-stabilized emulsions containing both oil and aqueous phases, edible oils such as vegetable oil, olive oil, corn oil, soybean oil, canola oil, sunflower seed oil, peanut oil, sucrose fatty acid polyesters, and the like can be used. Other edible oils may also be used. A single edible oil or mixtures of such edible oils may be used.

If desired, large amounts of plant sterols and/or plant sterol esters (i.e., up to about 50 percent of the total mesophase) can be incorporated into these compositions. In some cases, however, the amount of plant sterols and/or plant sterol esters may be present at higher levels of the mesophase gel. In such cases, the excess plant sterol and/or plant sterol esters may incorporated into the mesophase-stabilized emulsion during the application of shear. Alternatively, such excess plant sterol and/or plant sterol esters can be incorporated into the mesophase-stabilized emulsion by adding oil during the application of shear; of course, such added oil will increase the oil content of the resulting product. Shear in these processes should normally be in the range of about 5000 $sec^{-1}$ to about 50,000 $sec^{-1}$.

Mixtures of emulsifiers and water can form a number of different physical structures depending on emulsifier to water ratios, types of (including their HLB values) and amounts of emulsifiers, process variables (e.g., temperature, shear rates, order of component additions, and the like), and like variables. Such mixtures are generally opalescent dispersions referred to as liquid crystals or mesophases. A mesophase is a structure that may be manifested in several forms such as lamellar, vesicular, cubic and hexagonal forms, depending upon the emulsifiers used, the emulsifier to water ratio and the conditions used. These mesophase structures are described in *Bailey's Industrial Oil and Fat Products*, Vol. 3, pages 499–502 (1996). An emulsifier such as a diacetyl tartaric ester of monoglyceride, when dispersed in water, crystallizes in bilayers, with the thickness of each bilayer defined by the length of the two monoglyceride molecules oriented end to end. When heated in water, the fatty acid chains gain thermal mobility and lose their ordered structure, and the solvent, water, intrudes between the bilayers. Under proper conditions of temperature and solvent content, this intrusion results in the formation of a lamellar mesophase. At higher water levels and within a certain temperature range, the lamellar mesophase may be transformed into spherical multilamellar vesicles or liposomes. Such an aqueous solution of emulsifier(s) dissolved in water and forming a mesophase complex is known as a mesophase gel.

The inclusion of oil and plant sterol(s) or plant sterol ester(s) with emulsifier(s), when dispersed in an oil emulsifier phase, and an aqueous phase with emulsifier(s) dispersed therein is added to the oil emulsifier phase, and such mixture is subjected to shear under the conditions describe herein, results in a mesophase dispersed in an emulsion. The present invention includes such emulsions stabilized by mesophases dispersed therein. Some of the compositions disclosed herein are thus mesophases dispersed within emulsions, and are, in fact, mesophase-stabilized emulsions.

Alternatively, a dispersion within the mesophase results upon the inclusion of non-oil ingredients in the mesophase gel. Such a mesophase gel-stabilized dispersion is comprised of relatively low levels of cholesterol-reducing-compounds (generally at about 1 to about 6 percent based on the total weight of the composition), an aqueous phase, two or more emulsifiers, edible acids, flavorings, egg products, and the like. When subjected to shear under the conditions desired herein, such a mixture will result in dispersions stabilized by the mesophase. Such cholesterol-reducing-compounds containing mesophase-stabilized dispersions may be utilized to produce fat-free and triglyceride-free food products.

The hydrophile-lipophile balance (HLB) values of the emulsifiers used in the present invention appears to be critical in the formation of such stable mesophase-stabilized emulsions and dispersions. For a given oil and water system, there is an optimum balance between molecular hydrophilic and lipophilic character which leads to maximum emulsification efficiency. Emulsifiers with low HLB numbers (i.e., in the range of about 2 to about 6) are suitable for preparing water-in-oil emulsions; those with high HLB numbers (i.e., in the range of about 9 to about 22) are suitable for oil-in-water emulsions; and those with intermediate or medium HLB numbers (i.e., in the range of about 6 to about 9) are suitable for either type of emulsion depending upon ratio of oil and water, temperature and other conditions. HLB values for a given emulsifier may be determined experimentally by the method originally described by W. C. Griffin, *J. Soc. Cosmetic Chem.*, 1, 311 (1949). Or they may be calculated using the formula of J. T. Davies, *Proc. 2nd Int. Cong. Surface Activity*, vol. 1, p. 426 (1957):

$$HLB = 7 + \sum_i n_H(i) - \sum_j n_L(j)$$

where $n_H(i)$ and $n_L(j)$ are empirically-derived individual group numbers for the hydrophilic groups (i) and lipophilic groups (j) assigned by Davies.

Using the Davies method, calculated HLB values for especially preferred emulsifiers useful in this invention are as follows: diacetyl tartaric acid monostearate glyceride (DATEM), HLB 8, monoglyceride (MG), HLB 3; sucrose monostearate (SMS), HLB 16; and sodium stearoyl lactylate (SSL), HLB 21. It should be noted that group numbers for charged residues depend on the ionic strength of the aqueous phase Therefore, although the calculated HLB value for sodium stearoyl lactylate is 21, an experimentally derived HLB value would be closer to 12; either of these values fall within the required range for the third emulsifier.

The mesophase compositions of the present invention contain two or three distinct types of emulsifiers having different HLB values. It appears that the emulsifiers can be co-crystallized into a complex. The preparation of mesomorphic phases for use in food products has been described, for example, in U.S. Pat. No. 5,652,011 and European Patent Publication EP 0 558 523 B2. However, these publications do not utilize plant sterols and/or plant sterol esters to generate cholesterol-reducing mesophase-stabilized compositions as the present invention does.

For use in the present invention, emulsifier A has an intermediate HLB of about 6 to 9. Examples of such emulsifiers include, but are not limited to, a diacetyl tartaric acid ester of a monoglyceride (DATEM), sorbitan monopalmitate,, sorbitan monolaurate, and polyoxyethylene stearic acid monoester. Preferably, emulsifier A is DATEM. The fatty acid group of the diacetyl tartaric acid ester of a monoglyceride can be, for example, selected from the group consisting of saturated and unsaturated $C_6$–$C_{22}$ fatty acids.

Especially preferred saturated fatty acids are stearic acid and palmitic acid; especially preferred unsaturated fatty acids are long chain ($C_{16}$–$C_{22}$) trans unsaturated fatty acids.

Emulsifier B has a low HLB of about 2 to 6. Examples of such emulsifiers include, but are not limited to, monoglycerides (MG), glycerol monostearate, sucrose distearate, sorbitan monostearate, glycerol monolaurate, and ethylene glycol monostearate. Preferably emulsifier B is a monoglyceride. The fatty acid of the monoglyceride can also selected from the group consisting of saturated and unsaturated $C_6$–$C_{22}$ fatty acids. Especially preferred saturated fatty acids for the monoglyceride are stearic acid and palmitic acid. Especially preferred unsaturated fatty acids are long chain ($C_{16}$–$C_{22}$) saturated fatty acids.

Emulsifier C has a high HLB of about 9 to 22. Examples of such emulsifiers include, but are not limited to, sucrose monostearate, sodium stearoyl lactylate (SSL), sucrose monolaurate, polyoxyethylene sorbitan monopalmitate, or polyoxyethylene stearic acid monoester. Preferably emulsifier C is sodium stearoyl lactylate. The fatty acid components of the third emulsifier can also be selected from the group consisting of saturated and unsaturated $C_6$–$C_{22}$ fatty acids. Preferred saturated fatty acids are stearic acid and palmitic acid. Preferred unsaturated fatty acids are long chain ($C_{16}$–$C_{22}$) trans unsaturated fatty acids.

Key considerations, in addition to the HLB values, in the selection of suitable emulsifiers are their melting point and crystallization characteristics. Preferably, the emulsifiers have melting points above about 37° C. Such melting points allow these emulsifiers to be added in powder form to the liquid phases of the invention. These emulsifiers easily crystallize upon cooling to temperatures below their melting point. With such characteristics, the lamellar nature of the mesophase gels and mesophase-stabilized emulsions of the present invention are stabilized upon cooling. The fatty acid groups can be modified or changed in the various emulsifiers to obtain the desired characteristics.

For example, emulsifiers containing typical cis unsaturated fatty acids often have very low melting points (e.g., below about 30° C.) and would not generally be suitable for incorporation in mesophase-stabilized emulsions intending to be used in food products to be used at ambient temperature (e.g., spoonable dressings, whipped toppings, cream cheese, and similar products). Such very low melting emulsifiers would likely disrupt the crystal packing and destroy the lamellar nature of the mesophase complexes which appear to be present in such mesophase-stabilized emulsions unless they are handled and stored at very low temperatures. However, for some applications (e.g., frozen desserts, frozen dairy foods, and other low temperature food products), such low melting emulsifiers could, if desired, be used, and, in some cases, may even be preferred.

When mesophase-stabilized emulsions and dispersions are prepared as described herein, they appear to be very stable; in many cases, no syneresis is evident even after prolonged (i.e., periods of 12 months or even longer storage at ambient temperatures). The present mesophase-stabilized emulsions and dispersions remain stable even when subjected to harsh conditions. Centrifugation of conventional (i.e., non-mesophase-stabilized) emulsions will often result in the destruction or breaking down of the emulsion due to flocculation and coalescence of oil droplets; in such cases, an oil phase upper layer and an aqueous phase lower layer, often with a clear interface between the two phases, is formed. Likewise, very long-term storage of a conventional low-fat emulsion stabilized with the addition of polysaccharide components will often result in a breakdown of the emulsion into an aqueous phase and an oil phase. In contrast, the mesophase-stabilized emulsions described herein are very stable when subjected to harsh treatment (e.g., centrifugation) or when stored for long periods of time In some instances, however, the mesophase-stabilized emulsions of the present invention separate into an oil emulsion and a mesophase gel under harsh centrifugation-like conditions. Nonetheless, these mesophase-stabilized emulsions are still advantageous with respect to stability as compared to foods prepared with low-fat emulsions that have been stabilized with starches or other polysaccharides. Where a mesophase gel is formed upon centrifugation, the use of certain emulsifier ratios, oil to water ratios, temperatures, order of addition of components and different process conditions, are some of the factors that control whether the mesophase gel is stable. This stability is indicated by little or no water separating from the gel. Likewise, in instances in which the mesophase-stabilized emulsion separates into an oil emulsion and a mesophase gel under harsh centrifugation conditions, the oil emulsion which separates from the mesophase gel generally remains stable. Thus, little or no oil is released from the oil emulsion upon centrifugation.

Factors such as oil to emulsifier ratio, water to emulsifier ratio, oil to water ratio, temperature, the specific emulsifiers used and their ratios, the order of addition of components and the phase in which each emulsifier is dispersed (i.e., dispersion of the intermediate HLB emulsifier and low HLB emulsifier in oil or water, dispersion of the high HLB emulsifier in water) and process factors such as shear, control the stability of the mesophase-stabilized emulsions generated as described herein. Some mesophase-stabilized emulsions remain wholly as a mesophase-stabilized emulsion under centrifugation conditions Others form relatively stable oil emulsions. Others form relatively stable mesophase gels upon centrifugation treatment.

In addition to centrifugation analysis as discussed above, light microscopy can be used to evaluate the relative stability of the mesophase-stabilized emulsions described herein. Using light microscopy, an array of relatively small oil droplets in a narrow range size distribution is indicative of a stable emulsion, as the oil is relatively evenly dispersed in the aqueous phase of the oil-in-water emulsion. Such an emulsion is less likely to break and form an oil phase and an aqueous phase under centrifugation or long term storage.

The cholesterol-reducing-compound-containing mesophase-stabilized compositions formed using two or three emulsifiers as detailed herein often show stability at room temperature of periods of a year or more. Some of the mesophase-stabilized emulsions and dispersions of the present invention retained their integrity as a mesophase-stabilized composition even when subjected to a harsh treatment such as centrifugation. Such a mesophase-stabilized emulsion is likely to maintain its integrity as an emulsion during prolonged storage at room temperature. Thus, the present cholesterol-reducing-compound-containing mesophase-stabilized compositions represent a considerable advantage over conventional low-fat emulsions.

Other characteristics of the present invention have been evaluated. The mesophase-stabilized compositions of the invention have been tested Theologically to determine yield stress in τ[Pa]. Measurements of yield stress may be made with conventional instruments such as, for example, a Haake VT 550 (Haake, Karlsruhe, Germany). Yield stress may be interpreted as an indication of the degree of gelation of the emulsion. Intuitively, it is desirable to have relatively higher yield stress characteristics for food products such as spoonable dressings, whipped toppings, whipped desserts, sour cream products, cream cheese products, spreads and the like, and relatively low values for pourable dressings, sauces and the like. As illustrated in Example 2 of our copending application, the yield stress of the different formulations of mesophase-stabilized compositions was observed prior to centrifugation. Using the guidance provided in this specification, and that of the copending application, one can prepare suitable food products containing the mesophase-stabilized emulsions or dispersions containing cholesterol-reducing-compounds using routine experimentation The optimal yield stress characteristics for cream cheese products, spreads and the like, appears to be from about 800 to about 2000 τ[Pa] and more preferably from about 1200 to about 1600 τ[Pa]. The optimal yield stress characteristics for spoonable dressings, whipped toppings, whipped desserts, sour cream products and the like appears to be from about 180–260 τ[Pa], and more preferably about 200–240 τ[Pa]. In contrast, sauces, pourable dressings and the like would optimally have a yield stress of about 80–150 τ(Pa), and more preferably about 100–120 τ(Pa).

The viscosities of the different formulations of cholesterol-reducing-compound-containing mesophase-stabilized compositions may be measured with a conventional instrument that detects viscosity, such as a Bohlin Visco 88 viscometer at 50 sec$^{-1}$ (Bohlin, Lund, Sweden). As illustrated in Example 2 of our copending application, the viscosity of the different formulations of mesophase-stabilized compositions was observed prior to centrifugation. Using the guidance provided in this specification and that of the copending application, one can prepare suitable food products containing the cholesterol-reducing-compound-containing mesophase-stabilized compositions using routine experimentation. For spoonable dressings, whipped toppings, whipped desserts, sour cream products and the like, the optimal viscosity would be between about 4.0 and about 6.0 Pas and preferably, between about 4.4 and about 5.6 Pas. For a pourable dressing or sauce, the optimal viscosity would be between about 0.5 and about 2.0 Pas and preferably, between about 0.8 and about 1.4 Pas.

The oil to emulsifier ratio, water to emulsifier ratio, oil to water ratio, cholesterol-reducing compound to emulsifier ratio, cholesterol-reducing-compounds to water ratio, temperature, order of addition of components, phase in which they are dispersed (i.e., dispersion of DATEM and MG in oil or water, SSL in water), process factors such as shear, the specific emulsifiers used and their ratios, are all factors that can be controlled to result in emulsions or dispersions which, when combined with other food product components, yield desirable product characteristics. Our copending application, and especially the Tables in Example 2 therein, provide detailed guidance on the variations of these factors (except, of course, those involving the cholesterol-reducing-compounds). Using the guidance provided in this specification and that of the copending application, one can prepare suitable food products containing mesophase-stabilized emulsions or dispersions containing cholesterol-reducing-compounds using routine experimentation.

Optimal ranges of emulsifiers (and the ratios which can be derived from them) which provide excellent characteristics for a particular product application (i.e., spoonable dressings or, alternatively, pourable dressings) have been determined. For cholesterol-reducing-compound-containing-compositions formulated using emulsifiers A, B, and C, the emulsifier level of emulsifier A ranges from about 1 to about 40 percent of the total emulsion composition; emulsifier B ranges from about 20 to about 60 percent of the total emulsifier composition, and emulsifier C ranges from about 10 to about 60 percent of the total emulsifier composition. Alternatively, for compositions formulated using emulsifiers A and C, the emulsifier level of emulsifier A ranges from about 25 to about 75 percent and emulsifier C ranges from about 25 to about 75 percent of the total emulsifier composition. For compositions formulated using emulsifiers B and C, the emulsifier level of emulsifier B ranges from about 25 to about 75 percent of the total emulsifier composition, and emulsifier C ranges from about 25 to about 75 percent of the total emulsifier composition.

In addition, data presented in Example 2 of our copending application indicate that, for compositions formulated using three emulsifiers, the following ranges of emulsifier composition may be found optimal for different applications. To optimize yield stress, and to optimally prepare an emulsion or dispersion for use in a spoonable dressing, for instance, one preferred emulsifier mixture includes about 20 to about 40 percent diacetyl tartaric acid ester of a monoglyceride (DATEM), about 40 to about 60 percent monoglyceride (MG), and about 10 to about 30 percent sodium stearoyl lactylate (SSL). To optimize viscosity, and to optimally prepare an emulsion or dispersion for use in a sour cream product, for instance, one preferred emulsifier mixture includes about 20 to about 40 percent DATEM, about 20 to about 40 percent MG, and about 30 to about 50 percent SSL. Alternatively, to optimize aqueous stability, and to best prepare a pourable dressing, for example, one preferred emulsifier mixture includes about 5 to about 25 percent DATEM, about 20 to about 50 percent MG, and about 4%) to about 60 percent SSL. Of course, one skilled in the art will realize that other emulsifiers (having the required HLB values) and other ranges of the three emulsifiers can be used, and in some cases, may even be preferred.

In one embodiment of the invention, the emulsifier A, preferably in dry powder form, and emulsifier B, preferably in dry powder form, are dispersed in the oil phase at room temperature and then heated to about 80° C. to about 100° C. to form the oil emulsifier phase. More preferably, the oil phase is heated to between about 85° C. and about 95° C. most preferably, the oil emulsifier phase is heated to about 90° C. The cholesterol-reducing-compound is added to the heated oil emulsifier phase containing emulsifiers A and B. Emulsifier C, preferably in dry powder form, is dispersed in water (generally at about 20 to about 35° C. and preferably at or close to room temperature) to form the aqueous emulsifier phase. The oil emulsifier phase is then poured slowly into the aqueous emulsifier phase while mixing, producing a mixture or a coarse emulsion. The coarse emulsion is cooled and maintained at between about 40° C. and about 55° C. and preferably at between about 45° C. and about 50° C. The coarse emulsion is then homogenized through a moderate to high shear device. Moderate to high shear, for purposes of this invention, is generally between about 5000 sec$^{-1}$ and about 50,000 sec$^{-1}$. Preferably, the shear used is between about 15,000 sec$^{-1}$ and about 25,000 sec$^{-1}$. The consistency of a mesophase-stabilized emulsion thus generated containing about 6% total emulsifier and about 30% oil is that of heavy cream at about 45° C. to about 50° C. The resulting mesophase-stabilized emulsion is then stored at refrigeration temperature (i.e., about 2° C. to about 8° C. and preferably, about 5° C. to about 6° C.). After overnight storage at refrigeration temperature, the cholesterol-reducing-compound-containing mesophase-stabilized emulsion generally sets up to a consistency of sour cream. Alternatively, the emulsion may be cooled to refrigeration temperature in a heat exchanger, which results in rapid production (e.g., within about 2–20 minutes) of a product with the consistency of sour cream.

In another embodiment of the invention, two emulsifiers are preferably used. In this embodiment, either emulsifier A or emulsifier B, preferably in dry powder form, is disperse in the oil phase at room temperature, then heated to between about 80° C. and about 100° C. to form the oil emulsion phase. More preferably, the oil emulsifier phase is heated to between about 85° C. and about 95° C.; most preferably, the oil phase is heated to about 90° C. The cholesterol-reducing compound is added to the heated oil emulsifier phase containing either emulsifier B or emulsifier C. Emulsifier C, preferably in dry powder form, is dispersed in room temperature water to form the aqueous emulsifier phase. The oil emulsifier phase is then poured slowly into the aqueous emulsifier phase while mixing, producing a mixture or coarse emulsion. The coarse emulsion is then homogenized through a moderate to high shear device. Moderate to high shear is defined here as being between about 5000 $sec^{-1}$ to about 50,000 $sec^{-1}$. Preferably, the level of shear used is between about 15,000 $sec^{-1}$ and about 25,000 $sec^{-1}$. The resulting cholesterol-reducing-compound-containing mesophase-stabilized emulsion is then set by cooling at refrigeration temperatures for several hours (i.e., about 2° C. to about 8° C. and preferably, about 5° C. to about 6° C.) to allow complete formation of the liquid crystalline mesophase. Alternatively, the mesophase-stabilized composition may be set by rapidly cooling while passing the gel through a heat exchanger.

In another embodiment of the invention, emulsifiers A, B and C, in powder form are preferably blended together and added to an aqueous phase. If emulsifiers A, B and C are added individually to the aqueous phase, the mixture does not form a mesophase gel. Preferably the blend of emulsifiers is in dry powder form. If desired, an emulsifier with a relatively low melting point may be frozen and ground to a powder while frozen. The mixture of emulsifiers is added to the aqueous phase at a level of about 1 to about 15 percent of the mesophase-stabilized composition and then dispersed at room temperature with stirring to form an aqueous emulsifier phase. The aqueous emulsifier phase is then heated to above the melting temperature of the emulsifiers, generally about 60° C. to about 90° C. with stirring and held at that temperature with stirring for several minutes. Preferably, the cholesterol-reducing compound is melted and added to the aqueous emulsifier phase with stirring. The mixture is then cooled to between about 20° C. and 90° C. The dispersion is subjected to high shear at about 5000 $sec^{-1}$ to about 50,000 $sec^{-1}$ to form a mesophase gel. The resulting mesophase can be set by cooling at refrigeration temperatures for several hours (i e., about 2° C. to about 25° C. and preferably, about 5° C. to about 6° C.) to allow complete formation of the liquid crystalline mesophase. Alternatively, the mesophase gel may be set rapidly by cooling while passing the gel through a heat exchanger.

In still another embodiment of the invention, either emulsifiers A and C, or, alternatively, Emulsifiers B and C are preferably blended together and added to an aqueous phase. Again, as in the previous embodiment, preferably the blend of emulsifiers is in dry powder form. The mixture of emulsifiers is added to the aqueous phase at a level of about 1 to about 15 percent of the mesophase-stabilized emulsion and then dispersed at room temperature with stirring to form the aqueous emulsion phase. The aqueous solution with dispersed emulsifiers is then heated to above the melting temperatures of the emulsifiers, optimally to about 60° C. to about 90° C. while stirring and held at that temperature with stirring for several minutes. Preferably, the cholesterol-reducing compound is melted and added to the dispersed emulsifiers with stirring. The mixture is then cooled to between about 20° C. and about 90° C. The dispersion is subjected to high shear at about 5000 $sec^{-1}$ and about 50,000 $sec^{-1}$ to form a mesophase gel. The resulting mesophase may be set by cooling at refrigeration temperatures for several hours (i.e., about 2° C. to about 25° C. and preferably, about 5° C. to about 6° C.) to allow complete formation of the liquid crystalline mesophase. Alternatively, the mesophase gel may be set rapidly by cooling while passing the gel through a heat exchanger.

In yet two other embodiments of the invention, a mixture of emulsifiers selected from the group consisting of (1) emulsifiers A, B, and C; (2) emulsifiers A and C; (3) emulsifiers B and C, are blended together, preferably in dry powder form, and added to an aqueous liquid. The emulsifier mixture is added to the aqueous phase at a level from about 1 to about 15 percent of the mesophase-stabilized composition and then dispersed at room temperature with stirring to form the aqueous emulsifier phase. The aqueous emulsifier phase is then heated to above the melting temperature of the emulsifiers, generally about 60° C. to about 90° C., with stirring and held at that temperature with stirring for several minutes. Preferably, the cholesterol-reducing-compound is melted and added to the aqueous emulsifier phase with stirring. This mixture is then heated to a temperature range of about 80° C. to about 100° C., and subsequently cooled to a temperature range of about 45° C. to about 90° C. with mixing. The dispersion is subjected to high shear at about 5000 $sec^{-1}$ to about 50,000 $sec^{-1}$ to form a mesophase dispersion or emulsion. There is no detectable difference in characteristics between mesophase gels prepared as described for these two embodiments and for mesophase gels prepared as described for the preceding two embodiments.

If a relatively (i.e., less than 6 percent) small amount of cholesterol-reducing-compound is utilized in the four embodiments herein described to which no oil phase is added, a mesophase gel is formed. Such a cholesterol-reducing-compound-containing mesophase gel may be converted to a cholesterol-reducing-compound-containing mesophase-stabilized emulsion by adding oil to the gel and then processing in a conventional food processor such as a Cuisinart® operated at a medium to high speed or in a rotor-stator shear device. Thus, adding oil to the mesophase gel under moderate shear conditions, results in the formation of a mesophase-stabilized emulsion The formation of the mesophase-stabilized emulsion of this embodiment may take place at temperatures ranging between about 5° C. and about 50° C. The mesophase-stabilized emulsion has the consistency of a spoonable dressing, such as mayonnaise. A low-fat spoonable dressing can be prepared adding salt, sugar, edible acids, and, optionally, egg products, to the mesophase-stabilized emulsion. The resulting product has the desired consistency of a spoonable dressing, and appears to be stable. No syneresis or oil separation is observed for up to 12 months when stored in a closed jar at room temperature.

Alternatively, the mesophase gel prepared as described herein may be used in the preparation of fat-free food products. To this end, flavorings, dairy products, egg products, acidic components and/or other food components may be added to the gel with stirring to produce a variety of fat-free food products.

Many conventional mixing or shearing devices can be used to prepare the mesophase-stabilized emulsions of this invention. Suitable devices include, for example, colloid mills and homogenizers Specific devices which have been used successfully include, Pentax™ KMF-15 (Bran-Luebbe, Buffalo Grove, Ill.), Ross™ mixers (Charles Ross & Sons, Co., Hauppauge, N.Y.), Oakes™ mixer (Oakes, Hauppauge, N.Y.), and Hydroshear™ mixers (APV Gaulin, Wilmington, Mass.). Of course, other specific devices could be used so long as they delivery the desired shear.

The Examples that follow and illustrate the invention are intended to further describe and not to limit the invention. The mesophase-stabilized emulsions and mesophase-stabilized dispersions of the present disclosure may be used to generate a variety of low-fat products (e.g., spoonable dressings, pourable dressings, sauces, whipped toppings, whipped desserts, cream cheese products, dips, yogurts, spreads, sour cream products, frozen desserts, frozen dairy products, and the like). All percentages used herein are by weight, unless otherwise indicated. All references cited in the present specification are incorporated by reference.

In the following Examples, emulsifier A is a 70/30 mixture of DATEM and monoglyceride (MG). Often emulsifier B is distilled monoglyceride. For purposes of this invention, the DATEM/MG blend is considered to be a single emulsifier. If desired, the amount of distilled MG could be corrected to take into account the MG present in the DATEM/MG blend. Often emulsifier C is sodium stearoyl lactylate.

EXAMPLE 1

Incorporation of 5% Stanol Ester into Mesophase Gel

In this first example, 5% stanol esters were incorporated into a mesophase gel which contained 6% total emulsifier.

| Ingredient | Percent | Weight (g) |
|---|---|---|
| Distilled monolyceride | 1.8 | 9.0 |
| DATEM/MG (70:30) | 1.8 | 9.0 |
| Sodium stearoyl lactylate | 2.4 | 12.0 |
| Stanol ester | 5.0 | 25.0 |
| Water | 89.0 | 445.0 |
| Total | 100 | 500 |

The three emulsifiers were dry blended and then dispersed in water in a beaker. The mixture was heated to 85° C. and held at that temperature for 20 minutes with continuous mixing by an overhead stirrer. Stanol ester was melted and added slowly into the emulsifier mixture at 85° C. Stanol ester was prepared from tall oil from pine trees which was hydrogenated and esterified with fatty acids from soybean oil. After all the stanol ester was incorporated into the mixture, the mix was cooled slowly with mixing to below 60° C., and then to room temperature (approximately 20° C.) without mixing. The resulting gel was homogenized using a colloid mill with a 5μ gap setting.

The product was very smooth and creamy. After refrigeration at 5° C. for 24 hours, the yield stress was determined with a Haake VT-550 to be 650 τ(Pa).

EXAMPLE 2

Incorporation of 10% Stanol Ester with 10% Oil into Mesophase Emulsion

In this Example, 10% stanol esters were incorporated along with 10% soybean oil into a mesophase emulsion which contained 6% total emulsifier.

| Ingredient | Percent | Weight (g) |
|---|---|---|
| Distilled Monoglyceride | 1.8 | 9.0 |
| Datem/MG (70:30) | 1.8 | 9.0 |
| Sodium Stearoyl Lactylate | 2.4 | 12.0 |
| Soybean Oil | 10.0 | 50.0 |
| Stanol Ester | 10.0 | 50.0 |
| Water | 74.0 | 370.0 |
| Total | 100 | 500 |

The three emulsifiers were dry blended and then dispersed in water in a beaker Under continuous mixing with an overhead stirrer, the mixture was heated to 85° C. Stanol ester was melted in the soybean oil. The stanol/oil mixture was added slowly into the emulsifier mixture at 85° C. and held at that temperature for 10–15 minutes. After all the stanol ester was incorporated, the mixture was cooled slowly with mixing to below 70° C. The emulsion was homogenized at 70° C. using a medium shear rotor/stator device at a rate of about 25000 sec$^{-1}$. The mixture was cooled to room temperature.

The resulting product was very smooth and creamy, and displayed no grittiness. Light microscopy showed that the product was a mesophase-stabilized emulsion with oil droplet size on the 2–10μ size range.

EXAMPLE 3

Incorporation of Higher Levels of Stanol Ester with 10% Oil into Mesophase Emulsion In this Example, higher levels of stanol esters in soybean oil were incorporated into a mesophase-stabilized emulsion which contained 6% total emulsifier.

| Ingredient | Weight (g) (15% Stanol) | Weight (g) (20% Stanol) | Weight (g) (30% Stanol) |
|---|---|---|---|
| Distilled Monoglyceride | 9.0 | 9.0 | 9.0 |
| DATEM/MG (70:30) | 9.0 | 9.0 | 9.0 |
| Sodium Stearoyl Lactylate | 12.0 | 12.0 | 12.0 |
| Soybean Oil | 50.0 | 50.0 | 50.0 |
| Stanol Ester | 75.0 | 100.0 | 150.0 |
| Water | 345.0 | 320.0 | 270.0 |
| Total | 500 | 500 | 500 |

The procedure was the same as in Example 2. The 15% and 20% stanol products were creamy and thick, smooth, and displayed no grittiness. Microscopy showed a mesophase-stabilized emulsion, although the droplet size was larger and more irregular than the 10% stanol product of Example 2. The 30% stanol mesophase emulsion could not be formed. It started to become very thick while it was being made, and then the emulsion broke, releasing the free oil and stanol ester.

EXAMPLE 4

Incorporation of 10% Stanol Ester into Mesophase Gel with No Added Oil

This example illustrates the preparation of 10% stanol ester in mesophase without an oil carrier. The following ingredients were used.

| Ingredient | Percent | Weight (g) |
|---|---|---|
| Distilled Monolyceride | 1.8 | 9.0 |
| DATEM/MG (70:30) | 1.8 | 9.0 |
| Sodium stearoyl Lactylate | 2.4 | 12.0 |
| Stanol Ester | 10.0 | 50.0 |
| Water | 74.0 | 420.0 |
| Total | 100 | 500 |

The three emulsifiers were dry blended and then dispersed in water in a beaker. Under continuous mixing with an overhead stirrer, the mixture was heated to 75° C. Stanol ester was melted and added slowly into the emulsifier mixture at 75° C. After all the stanol ester was incorporated, the mixture was heated to 90° C., held at that temperature for 5–10 minutes, and then cooled slowly with mixing to 70° C. using a medium shear rotor/stator device at a shear rate of 25,000 sec$^{-1}$. The mixture was cooled under refrigeration to 5° C.

The product was very smooth and creamy and displayed no grittiness.

EXAMPLE 5

Preparation of Cool Whip™ Type Frozen Whipped Topping Using Product of Example 4

The product of Example 4 was used to make a Cool Whip™ type of frozen whipped topping.

| Ingredient | Weight (g) |
|---|---|
| Stanol/Mesophase Gel | 100 |
| Sugar | 100 |
| Water | 100 |
| Nonfat Dry Milk | 30 |
| Cream Powder | 10 |
| Total | 340 |

The components were mixed with a Hobart™ mixer. It was then whipped for 3 minutes in the Hobart™ mixer to a final overrun of about 300%. ("Overrun" is the percentage increase in volume due to whipping.) The whipped topping product was transferred to covered bowls and stored in a freezer at −20° C. After freezing for 24 hours, one of the bowls was thawed under refrigeration (5° C.). The thawed product was very creamy, with a whipped cream-like texture. The product held up to refrigerator storage for 2 weeks without becoming "webby".

EXAMPLE 6

Preparation of Mesophase Gel or Mesophase-Stabilized Emulsion with Sterol Ester Two batches of plant sterol-containing mesophase-stabilized gels were made at pilot plant scale using the ingredients in the table below. Unlike the products of Examples 1–5 which were made with stanol esters, these products were made with plant sterol esters. The sterols were obtained from a soybean source and were esterified with fatty acids from soybean oil.

| Ingredient | Batch 1 Wt. (Lb.) | Batch 2 Wt. (Lb.) |
|---|---|---|
| Distilled Monoglyceride | 1.8 | 1.8 |
| DATEM/MG (70:30) | 1.8 | 1.8 |
| Sodium Stearoyl Lactylate | 2.4 | 2.4 |
| Soybean Oil | 10 | 0 |
| Sterol Ester | 10 | 30 |
| Water | 74 | 64 |
| Total | 100 | 100 |

The three emulsifiers were dry blended and then suspended in water in a jacketed tank with mixing by a surface scraper. The hydrated emulsifiers were heated with steam in the tank jacket up to 90° C. The emulsifier solution was maintained at this temperature for 10 minutes. In a separate tank, the sterol esters were melted at a temperature slightly above their melting temperature (65° C.). (For Batch 1, the melted sterol esters were then mixed with soybean oil. For Batch 2, the melted sterol esters were added directly to the hot emulsifier solution.) The (1) melted sterol ester/oil or (2) sterol ester mixture was added slowly to the hot emulsifier solution. The solution was cooled to 65° C., and then homogenized with a medium shear device at a shear rate of 20,000 sec$^{-1}$. The product was collected in plastic buckets (30 lb) and stored in a cooler at 5° C. for 24 hours.

The product was smooth in the mouth and displayed no grittiness. The flavor was typical of that of a soybean oil emulsion. Light microscopy revealed a very uniform emulsion with average droplet size of about 4μ. The yield stress was determined with a Haake VT-550. Batch 1 had a yield stress of 25 τ(Pa). Batch 2 had a yield stress of 343 τ(Pa).

EXAMPLE 7

Preparation of Mayonnaise-Type Dressing Product Using Mesophase Made with 30% Sterol Ester Batch 2 from Example 6 was used to prepare a spoonable mayonnaise-type dressing product using the following formulation.

| Ingredient | Percent | Wt. (g) |
|---|---|---|
| 30% Sterol/Mesophase | 92.63 | 277.9 |
| Salt | 1.65 | 4.95 |
| Sugar | 0.637 | 1.91 |
| Vinegar (120 grains) | 2.5 | 7.5 |
| Salted Liquid Yolk | 2.5 | 7.5 |
| Total | 100 | 300 |

Using a food processor, the sterol ester-containing mesophase-stabilized emulsion was mixed at low speed. The salt and sugar were added to the emulsion and the emulsion was mixed for one minute. Vinegar was added, followed by the salted egg yolk. The mayonnaise dressings were tested after 24 hours for stability and rheology. Yield stress was determined with a Haake VT 550 rheometer and viscosity was measured at 50 sec$^{-1}$ with a Bohlin Visco 88 viscometer. Stability was determined by a centrifugation test (100,000×G for 30 minutes). Released oil, released water and total emulsion were measured.

The product was stable, and had a yield stress value and viscosity typical of mayonnaise (about 225 τ(Pa) and 5.2 Pas, respectively).

EXAMPLE 8

Spoonable Salad Dressing with 10% Sterol Ester

This example illustrates the preparation of a spoonable salad dressing using the following formulation.

| Ingredient | Percent | Wt. (g) |
|---|---|---|
| Mesophase Emulsion (with 30% Sterol Ester) | 34 | 340 |
| Salt | 1.13 | 11.3 |
| Sugar | 7.589 | 75.8 |
| Spices | 0.6 | 6 |
| Vinegar 70 Grain | 5.7 | 57 |
| Cooked Starch Paste | 30.3 | 303 |
| Mesophase Emulsion (with 30% Soybean Oil) | 20.7 | 207 |

The procedure for preparing mesophase with sterol ester is illustrated in Example 6. The same procedure is applied to prepare the mesophase with soybean oil.

EXAMPLE 9

Vegetable-flavored Spread with 10% Sterol Ester

This Example illustrates the preparation of a vegetable spread with 10% sterol ester for bagels and breads. The following formulation was used.

| Ingredient | Percent | Wt (g) |
|---|---|---|
| Mesophase Emulsion (with 30% Sterol Ester) | 34 | 340 |
| Vinegar 120 Grain | 2.5 | 25 |
| Sugar | 0.63 | 6.3 |
| Puffed Dry Carrots and Spices | 0.77 | 7.7 |
| Mesophase Emulsion (with 30% Soybean Oil) | 62.1 | 621 |

The procedure for preparing mesophase with sterol ester is illustrated in Example 6. The same procedure is applied to prepare the mesophase with soybean oil.

EXAMPLE 10

Onion Sour Cream Ranch Pourable Dressing with 5% Sterol Ester

This example illustrates the preparation of an onion/sour cream ranch pourable dressing of the following formulation.

| Ingredients | Percent | Wt (g) |
|---|---|---|
| Mesophase Emulsion (with 30% sterol ester) | 16.6 | 166 |
| Buttermilk | 16.6 | 166 |
| Vinegar | 4.2 | 42 |
| Sugar | 2.99 | 29.9 |
| Salt | 1.43 | 14.3 |
| Dry Sour Cream | 2.0 | 20 |
| Spices and Flavors | 2.18 | 21.8 |
| Mesophase Emulsion (with 30% Soybean Oil) | 42.5 | 425 |
| Water | 11.5 | 115 |

The procedure for preparing mesophase with sterol ester is illustrated in Example 6. The same procedure is applied to prepare the mesophase with soybean oil. The above prototype products have shown an excellent textural and flavor attributes.

What is claimed is:

1. A cholesterol-reducing-compound-containing mesophase-stabilized composition for use in low-fat, fat-free and triglyceride-free food products comprising about one to about fifty percent of a cholesterol-reducing-compound, an aqueous phase and about one to about fifteen percent of an emulsifier mixture comprising a combination of emulsifiers selected from the group consisting of (1) emulsifiers A, B, and C, (2) emulsifiers A and C, and (3) emulsifiers B and C; wherein emulsifier A has an HLB value of about 6 to about 9; emulsifier B has an HLB value of about 2 to about 6; and emulsifier C has an HLB value of about 9 to about 22.

2. The cholesterol-reducing-compound-containing mesophase-stabilized composition as defined in claim 1, wherein the emulsifier mixture comprises emulsifiers A, B and C.

3. The cholesterol-reducing-compound-containing mesophase-stabilized composition as defined in claim 1, wherein the emulsifier mixture comprises emulsifiers A and C.

4. The cholesterol-reducing-compound-containing mesophase-stabilized composition as defined in claim 1, wherein the emulsifier mixture comprises emulsifiers B and C.

5. The cholesterol-reducing-compound-containing mesophase-stabilized composition as defined in claim 2, wherein the cholesterol-reducing compound is selected from the group consisting of a sterol, a sterol ester, a stanol and a stanol ester.

6. The cholesterol-reducing-compound-containing mesophase-stabilized composition as defined in claim 3, wherein the cholesterol-reducing compound is selected from the group consisting of a sterol, a sterol ester, a stanol and a stanol ester.

7. The cholesterol-reducing-compound-containing mesophase-stabilized composition as defined in claim 4, wherein the cholesterol-reducing compound is selected from the group consisting of a sterol, a sterol ester, a stanol and a stanol ester.

8. The cholesterol-reducing-compound-containing mesophase-stabilized composition as defined in claim 5, further comprising an oil phase.

9. The cholesterol-reducing-compound-containing mesophase-stabilized composition as defined in claim 6, further comprising an oil phase.

10. The cholesterol-reducing-compound-containing mesophase-stabilized composition as defined in claim 7, further comprising an oil phase.

11. A cholesterol-reducing-compound-containing mesophase-stabilized composition for use in low-fat food products comprising about one to about fifty percent of a cholesterol-reducing compound, an aqueous phase, an oil phase, and about one to about fifteen percent of an emulsifier mixture comprising a combination of emulsifiers selected from the group consisting of (1) emulsifiers A, B, and C; (2) emulsifiers A and C; and (3) emulsifiers B and C, wherein emulsifier A has an HLB value of about 6 to about 9; emulsifier B has an HLB value of about 2 to about 6; and emulsifier C has an HLB value of about 9 to about 22.

12. The cholesterol-reducing-compound-containing mesophase-stabilized composition as defined in claim 11, wherein the emulsifier mixture is emulsifiers A, B, and C.

13. The cholesterol-reducing-compound-containing mesophase-stabilized composition as defined in claim 11, wherein the emulsifier mixture is emulsifiers A and C.

14. The cholesterol-reducing-compound-containing mesophase-stabilized composition as defined in claim 11, wherein the emulsifier mixture is emulsifiers B and C.

15. The cholesterol-reducing-compound-containing mesophase-stabilized composition as defined in claim 12, wherein the cholesterol-reducing compound is selected from the group consisting of a sterol, a sterol ester, a stanol and a stanol ester.

16. The cholesterol-reducing-compound-containing mesophase-stabilized composition as defined in claim 13, wherein the cholesterol-reducing compound is selected from the group consisting of a sterol, a sterol ester, a stanol and a stanol ester.

17. The cholesterol-reducing-compound-containing mesophase-stabilized composition as defined in claim 14, wherein the cholesterol-reducing compound is selected from the group consisting of a sterol, a sterol ester, a stanol and a stanol ester.

18. A method for making a cholesterol-reducing-compound-containing mesophase-stabilized composition for use in low-fat and fat-free food products comprising:
 (a) forming an aqueous emulsifier phase by dispersing an emulsifier mixture in an aqueous phase;
 wherein the emulsion mixture is selected from the group consisting of (1) emulsifiers A, B, and C; (2) emulsifiers A and C, and (3) emulsifiers B and C, wherein emulsifier A has an HLB value of about 6 to about 9, emulsifier B has an HLB value of about 2 to about 6; and emulsifier C has an HLB value of about 9 to about 22;
 (b) heating the aqueous emulsifier phase to a range of temperatures between about 45° C. to about 90° C.;
 (c) melting a cholesterol-reducing-compound;
 (d) adding the melted cholesterol-reducing-compound to the aqueous emulsifier phase with mixing;
 (e) heating the product of step (d) to a temperature the range of about 80° C. to about 100° C. for a time sufficient to form a cholesterol-reducing-compound-containing mesophase-stabilized composition;
 (f) slowly cooling the product of step (e) to a temperature range of about 60° C. to about 75° C. with mixing; and
 (g) subjecting the product of step (f) to shear in the range of about 5000 sec$^{-1}$ to about 50,000 sec$^{-1}$;
 wherein the resulting product is the cholesterol-reducing-compound-containing mesophase-stabilized composition.

19. The method as defined in claim 18, wherein the emulsifier mixture is emulsifiers A, B, and C.

20. The method as defined in claim 18, wherein the emulsifier mixture is emulsifiers A and C.

21. The method as defined in claim 18, wherein the emulsifier mixture is emulsifiers B and C.

22. The method as defined in claim 19, wherein the cholesterol-reducing compound is selected from the group consisting of a, sterol, a sterol ester, a stanol and a stanol ester.

23. The method as defined in claim 20, wherein the cholesterol-reducing compound is selected from the group consisting of a sterol, a sterol ester, a stanol and a stanol ester.

24. The method as defined in claim 21, wherein the cholesterol-reducing compound is selected from the group consisting of a sterol, a sterol ester, a stanol and a stanol ester.

25. The method as defined in claim 22, wherein an oil phase is added with moderate shear to generate a cholesterol-reducing-compound-containing mesophase stabilized emulsion for use in low-fat food products.

26. The method as defined in claim 23, wherein an oil phase is added with moderate shear to generate a cholesterol-reducing-compound-containing mesophase stabilized emulsion for use in low-fat food products.

27. The method as defined in claim 24, wherein an oil phase is added with moderate shear to generate a cholesterol-reducing-compound-containing mesophase stabilized emulsion for use in low-fat food products.

28. A method for making a cholesterol-reducing-compound-containing mesophase-stabilized composition for use in low-fat food products comprising an emulsifier mixture selected from the group consisting of (1) emulsifiers A, B, and C; (2) emulsifiers A and C; and (3) emulsifiers B and C; wherein emulsifier A has an HLB value of about 6 to about 9; emulsifier B has an HLB value of about 2 to about 6; and emulsifier C has an HLB value of about 9 to about 22;
 (a) forming an aqueous emulsifier phase by dispersing the emulsifier mixture in the aqueous phase;
 (b) heating the aqueous emulsifier phase to a range of temperature between about 60° C. to about 90° C.;
 (c) melting a cholesterol-reducing-compound in the oil phase;
 (d) adding the product of step (c) to the aqueous emulsifier phase at a temperature in the range of about 75° C. to about 90° C. with mixing to form a coarse emulsion;
 (e) subjecting the product of step (d) to shear in the range of about 5000 sec$^{-1}$ to about 50,000 sec$^{-1}$ to form a cholesterol-reducing-compound-containing mesophase-stabilized emulsion; and
 (f) cooling the mesophase-stabilized emulsion formed in step (e) to a range of about 3° to about 20° C.

29. The cholesterol-reducing-compound-containing mesophase-stabilized composition as defined in claim 28, wherein the emulsifier mixture is emulsifiers A, B, and C.

30. The cholesterol-reducing-compound-containing mesophase-stabilized composition as defined in claim 28, wherein the emulsifier mixture is emulsifiers A and C.

31. The cholesterol-reducing-compound-containing mesophase-stabilized composition as defined in claim 28, wherein the emulsifier mixture is emulsifiers B and C.

32. The cholesterol-reducing-compound-containing mesophase-stabilized composition as defined in claim 29, wherein the cholesterol-reducing compound is selected from the group consisting of a sterol, a sterol ester, a stanol and a stanol ester.

33. The cholesterol-reducing-compound-containing mesophase-stabilized composition as defined in claim 30, wherein the cholesterol-reducing compound is selected from the group consisting of a sterol, a sterol ester, a stanol and a stanol ester.

34. The cholesterol-reducing-compound-containing mesophase-stabilized composition as defined in claim 31, wherein the cholesterol-reducing compound is selected from the group consisting of a sterol, a sterol ester, a stanol and a stanol ester.

35. A method for making a cholesterol-reducing-compound-containing mesophase-stabilized composition for use in low-fat food products comprising at least two emulsifiers, a cholesterol-reducing compound, an oil phase and an aqueous phase;
 (a) adding one or more emulsifiers selected from the group comprising (1) emulsifiers A and B; (2) emulsifier A; and (3) emulsifier B to the oil phase and mixing with heat to form an oil emulsifier phase; wherein emulsifier A has an HLB value of about 6 to about 9; emulsifier B has an HLB value of about 2 to about 6, and emulsifier C has an HLB value of about 9 to about 22;

(b) adding the cholesterol-reducing compound to the oil emulsifier phase;

(c) adding Emulsifier C to the aqueous phase to form an aqueous emulsifier phase;

(d) adding the oil emulsifier phase to the aqueous emulsifier phase to form a coarse emulsion; and;

(e) subjecting the coarse emulsion to shear at about 5000 sec$^{-1}$ to about 50,000 sec$^{-1}$ for a time sufficient to form a cholesterol-reducing-compound-containing mesophase-stabilized emulsion.

36. The method as defined in claim 35, wherein the one or more emulsifiers added to the oil phase is emulsifiers A and B.

37. The method as defined in claim 35, wherein the one or more emulsifiers added to the oil phase is emulsifier A.

38. The method as defined in claim 35, wherein the one or more emulsifiers added to the oil phase is emulsifier B.

39. The method as defined in claim 36, wherein the cholesterol-reducing compound is selected from the group consisting of a sterol, a sterol ester, a stanol and a stanol ester.

40. The method as defined in claim 37, wherein the cholesterol-reducing compound is selected from the group consisting of a sterol, a sterol ester, a stanol and a stanol ester.

41. The method as defined in claim 38, wherein the cholesterol-reducing compound is selected from the group consisting of a sterol, a sterol ester, a stanol and a stanol ester.

* * * * *